United States Patent
Durand et al.

(10) Patent No.: US 8,067,338 B2
(45) Date of Patent: Nov. 29, 2011

(54) TRICHLORO SILYL ALKYL ISOCYANATE MOLECULE AND SURFACE MODIFIED MINERAL SUBSTRATE

(75) Inventors: Jean-Olivier Durand, Palavas-les-Flots (FR); Aurore Perzyna, Bucy-le-Long (FR); Nicolas Ardes-Guisot, Reze (FR); Emmanuelle Riou, Garons (FR); Michel Granier, Teyran (FR)

(73) Assignees: Centre National de la Recherche Scientifique, Paris (FR); Universite de Montpellier, Paris (FR)

( * ) Notice: Subject to any disclaimer, the term of this patent is extended or adjusted under 35 U.S.C. 154(b) by 743 days.

(21) Appl. No.: 11/791,666

(22) PCT Filed: Nov. 28, 2005

(86) PCT No.: PCT/EP2005/013982
§ 371 (c)(1),
(2), (4) Date: May 28, 2008

(87) PCT Pub. No.: WO2006/056490
PCT Pub. Date: Jun. 1, 2006

(65) Prior Publication Data
US 2009/0023590 A1    Jan. 22, 2009

Related U.S. Application Data

(60) Provisional application No. 60/631,141, filed on Nov. 29, 2004.

(51) Int. Cl.
C40B 30/00 (2006.01)
C40B 50/18 (2006.01)
C40B 40/00 (2006.01)
C07F 7/10 (2006.01)

(52) U.S. Cl. .......... 506/7; 506/13; 506/32; 556/414
(58) Field of Classification Search .......... 506/7, 13, 506/32; 556/414
See application file for complete search history.

(56) References Cited

U.S. PATENT DOCUMENTS

| | | | |
|---|---|---|---|
| 5,624,711 A * | 4/1997 | Sundberg et al. | 506/32 |
| 2002/0106702 A1 * | 8/2002 | Wagner et al. | 435/7.9 |
| 2003/0082588 A1 * | 5/2003 | Garimella | 435/6 |

OTHER PUBLICATIONS

International Search Report for International Application No. PCT/EP2005/013982 dated Aug. 5, 2006.

* cited by examiner

*Primary Examiner* — Joseph Kosack
(74) *Attorney, Agent, or Firm* — William E. Beaumont

(57) ABSTRACT

A compound having formula (I):

$$X\text{—}E\text{—}Si\text{—}Cl_3 \qquad (I)$$

wherein:
X represents an isocyanate function;
E represents a straight, branched or cyclic alkyl chain comprising from 4 to 30 carbon atoms, and optionally contains a bridge function of —O—, —S—, —NH— or aryl;
and X and $SiCl_3$ are separated by a chain of at least 4 carbon atoms.

12 Claims, No Drawings

TRICHLORO SILYL ALKYL ISOCYANATE MOLECULE AND SURFACE MODIFIED MINERAL SUBSTRATE

The invention relates to new trichlorosilyl alkyl isocyanate molecules, to their use for the preparation of a device consisting of a mineral substrate with isocyanate groups grafted to its surface. Such a device and its use for immobilization of nucleophile function-containing molecules, preferably amino, hydroxyl or thiol group-containing molecules, on its surface, are another object of the invention, as well as its use for detection of a target molecule and/or screening of interaction with other molecules.

It has, in the recent years, become common practice to use inorganic/organic coupling agents to build an intermediate layer between an inorganic substrate and an organic matrix with the aim of preparing a device having immobilized molecules on its surface such as nucleic acids or proteins. Such devices are useful for the detection of target molecules in a sample.

Different methods for grafting an organic layer to the surface of a silica substrate are known: organization of the layer by physisorption, like for example using the well-known langmuir-blodgett method (G. Nonglaton, I. O. Benitez, I. Guisle, M. Pipelier, J. Léger, D. Dubreuil, C. Tellier, D. R. Talham, B. Bujoli, J. Am. Chem. Soc., 2004, 126, 1497); organization of the layer by chemisorption; grafting of an alkyl on a platinum substrate starting from an alcohol or amino function or grafting of an alkylthiol on a gold or silver substrate, or on an alumina substrate starting from a carboxylic acid function; grafting of organic molecules on a surface having free hydroxyl groups by building a covalent link, starting from organosilanes, like alkylalcoxysilanes or alkylaminosilanes (A. Ulman et al., Chem. Rev., 1996, 96, 1533-1554). It has also been known, from E. Lukevics et al., J. Am. Chem. Soc., 1999, 121, 12184, how to react organosilanes with molecules having a hydrogen giving reactive group such as acids, alcohols and thiols. This process however requires the use of a catalyst such as a Lewis base, or a nucleophile solvent.

It is also known, from WO 2003/006676, how to react an organotrialcoxysilane comprising an isocyanate terminal group with a surface having free hydroxyl groups. However, a trialcoxysilane, when reacted on such a surface has a reduced reactivity, requires harsh reaction conditions. Such a reactant can also lead to the production of aggregates, which give non reproducible results in a further screening application.

Thus it has been demonstrated by AFM in O. Melnyk et al., Bioconjug. Chem., 2004, 15, 317-325, that aminopropyl triethoxysilane, when grafted onto a glass plate produces about two layers of grafting.

No information regarding grafting homogeneity is given in WO 2003/006676. However it is clear from this document that grafting is three dimensional. Moreover, acid catalysis in a protic solvent like the method described in this document can lead to a partial hydrolysis of the isocyanate function and to other secondary reactions.

It has been an aim of the instant invention to remedy the drawbacks of the prior art and notably: to produce a molecule which can react with a mineral surface to produce an organic self organized bi-dimensional monolayer of an -alkyl-isocyanate type which can build a covalent link when reacted with a nucleophile group, like a hydroxyl or a thiol function, preferentially with an amino function.

The isocyanate group has been shown to be particularly important as coupling agent in a wide area of chemistry from materials engineering to biomolecules science (A. R. Katritsky, C. W. Rees, O. Meth-Cohn, Comprehensive Organic Functional Group Transformations 1995, Pergamon). Despite the importance of this group, very few examples of silica substrates functionalised with an isocyanate at the surface have been described, because this group is readily hydrolysed and condensed. Two approaches have been described so far.

The first one has been disclosed in WO 2003/006676 and is associated with the above-described drawbacks.

The second consists of reacting diisocyanates with the hydroxyl groups at the glass slide surface (Chun Y. S., Ha K., Lee Y. J., Lee J. S., Kim H. S., Park Y. S., Yoon K. B., Chem. Com. 2002, 1846), but the two isocyanate functions could be grafted, and harsh conditions (toluene 110° C.) were reported which limit the use of this procedure.

Trichlorosilanes have shown superior reactivity and better organization than trialkoxysilanes (Gauthier S., Aimé J. P., Bouhacian T., Attias A. J., Desbat B., Langmuir, 1996, 12, 5126; Ulman A., Chem. Rev., 1996, 96, 1533) for the preparation of self-assembled monolayers.

However, trichlorosilane alkyl isocyanates are almost unknown. Only three patents (U.S. Pat. No. 4,097,511; U.S. Pat. No. 3,511,866; DE 1938743) described the synthesis of trichlorosilylpropylisocyanate, its use in polymer chemistry is briefly reported, and only one publication from the sixties (Fan Y. L. et al., J. Org. Chem., 1973, 38, 2410) deals with this compound for the preparation of silylalkylperoxyde isocyanate.

It was not predictable from these documents that trichlorosilane alkylisocyanates could be used for grafting onto a mineral substrate and could produce a self assembled monolayer, with a bi-dimensional structure, while avoiding side reactions and degradation of the isocyanate function.

A first object of the instant invention is a molecule responding to formula (I):

$$X\text{-}E\text{-}SiCl_3 \qquad (I)$$

wherein:
X represents the isocyanate function —N=C=O,
E represents an alkyl chain, straight, branched or cyclic, comprising from 4 to 30 carbon atoms and wherein X and $SiCl_3$ are separated by a chain of at least 4, and preferably 10, carbon atoms.

This definition is meant to encompass:
alkyl chains of the type —$(CH_2)_n$— wherein $30 \geq n \geq 4$,
branched or cyclic chains of the type:

$$-(CH_2)n_1 - \left[ \begin{array}{c} CH \\ | \\ R_1 \end{array} \right]_{m_1} -(CH_2)n_2 - \left[ \begin{array}{c} CH \\ | \\ R_2 \end{array} \right]_{m_2} -(CH_2)n_3 - \cdots - \left[ \begin{array}{c} CH \\ | \\ R_j \end{array} \right]_{m_j} -(CH_2)n_j -$$

wherein:
j represents an integer selected from the group consisting of 1 ... 50;
$n_1, n_2 \ldots n_j$ independently represent an integer selected from the group consisting of 0 to 50;
$m_1 \ldots m_j$ are integers independently selected from 0, 1;
$R_1 \ldots R_j$ independently represent a $C_1$-$C_3$ alkyl group, and two consecutive $R_i$ groups can form a cycloalkyl together;

$\Sigma_{i=1}^{j} n_i + \Sigma_{i=1}^{j} m_i \geq 4$, preferably $$\Sigma_{i=1}{}^j n_i + \Sigma_{i=1}{}^j m_i \geq 8.$$

Moreover, this alkyl chain E can comprise a bridge function selected from the group consisting of: —O—, —S—, —NH—, —COO—, aryl.

According to a favourite variant of the invention E is a n-alkyl chain of the type —(CH$_2$)$_n$— wherein $30 \geq n \geq 4$.

Preferentially, $30 \geq n \geq 8$. Even more preferably, $25 \geq n \geq 10$.

The organotrichlorosilane of formula (I) can be prepared according to the following method: trichlorosilane is reacted with a 1-alkenylisocyanate in the presence of an organometallic catalyst, like Rh, Pd, Pt, Karstedt's catalyst, Speier's catalyst. Such a reaction is illustrated in detail in the experimental part. Karstedt's catalyst gives the best results and is the favourite catalyst to perform this reaction. The resulting product (I) is stable for months under inert atmosphere and is easy to handle.

In a second aspect, the invention is directed to a method for preparing a device comprising a mineral support (MS) and bound thereto a Self Assembled Monolayer (SAM) of molecules responding to formula (Ibis):

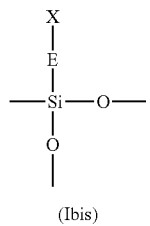

(Ibis)

wherein:

X and E have the same definition as in (I), and wherein X and Si are separated by a chain of at least 4 carbon atoms.

Said method is preferentially conducted in the following manner:

A mineral substrate comprising hydroxyl functions on its surface, preferably silanol functions, is reacted with a molecule of formula (I) in an aprotic solvent, preferentially in the presence of a Lewis base.

Among aprotic solvents which can be used in the method of the invention one can find: carbon tetra chloride, trichloroethylene, toluene and other weakly hygroscopic solvents. Triethylamine or diisopropylethylamine can be used as a Lewis base for this reaction.

As a mineral substrate comprising hydroxyl, and preferably silanol, functions on its surface one can use: wafer-type silicon covered by a layer of silica or a piece of glass. Other types of substrates are siliconized surfaces, germanium surfaces, mica, wave guides, nylon and silicon dioxide glass surfaces. A wafer-type silicon substrate can be obtained according to various methods:

A first method consists in removing the native silica layer by immersing the silicon substrate in a HF aqueous solution with a HF concentration of at least 10%, while submitting it to ultrasound treatment, rinsing with water followed by ozone treatment under UV. Such a preferred treatment is disclosed in J. R. Vig, J. Vac. Sci. Technol., 1985, 3, 1027-1034.

Another method consists in submitting the silicon substrate to an oxygen flow at an elevated temperature like for example 1 150° C., such as disclosed by D. L. Angst, Langmuir, 1991, 7, 2236-2242.

A third method consists in submitting the silicon substrate to a chemical basic oxidation: after cleaning the substrate's surface with a solvent and with application of ultra sounds, the substrate is left in a mixture of H$_2$O, NH$_4$OH, H$_2$O$_2$: 5/1/1, then rinsed with deionized water, dried and rehydrated, as disclosed in J. D. Legrange et al., Langmuir, 1993, 9, 1749-1753.

According to another method, the silicon substrate is submitted to a chemical acidic oxidation: the substrate is washed by a basic solution, then immersed in an acidic mixture such as H$_2$SO$_4$/H$_2$O$_2$, as taught by A. K. Kakka et al., Langmuir, 1998, 14, 6941-6947.

The same treatments can be applied to the glass substrate when such a substrate is used. A chemical acidic oxidation is the favourite treatment to be applied to a glass substrate.

Any type of silica surface can be used as a substrate including glass slides or particles, provided that its surface is covered by a layer of silica which has been deposited with any appropriate treatment. In the case of silica particles, one can refer for example to the method described in: B. L. Cushing, V. L. Koleshnichenko, C. J. O'Connor, Chem. Rev., 2004, 104, 3893.

The grafting reaction itself is performed in the following conditions:

The solution of organotrichlorosilane (I) is contacted with the mineral substrate. The organotrichlorosilane is solubilized in an aprotic solvent with a concentration preferably comprised between $10^{-3}$ to $10^{-1}$ mol/l. Solutions with a concentration comprised between 0, $5.10^{-2}$ mol/l and $5.10^{-2}$ mol/l are preferred.

The use of a secondary or tertiary amine, like preferably diisopropylethylamine (DIEA), in a quantity of 10 molar equivalents with regards to the quantity of organotrichlorosilane (1) avoids side reactions. In a favourite method, the substrate is immersed for a length of time of 15 minutes to 3 hours in the organotrichlorosilane solution comprising DIEA, preferably 30 minutes to 2 hours.

During the grafting reaction, the solution of organotrichlorosilane should be kept under controlled temperature. The appropriate temperature depends on the number of carbon atoms of the molecule (I). For example if E is C$_{18}$H$_{36}$ the temperature should be kept under 30° C. and if E is C$_{12}$H$_{24}$ the temperature should be kept under 10° C. Indications to select the best appropriate temperature are given in Brzoska et al., Langmuir, 1994, 10, 4367.

Preferably the grafting should be performed under inert atmosphere. The reaction of an organotrichlorosilane of formula (I) with a mineral substrate comprising hydroxyl functions on its surface can be described by scheme 1 here under:

Scheme 1

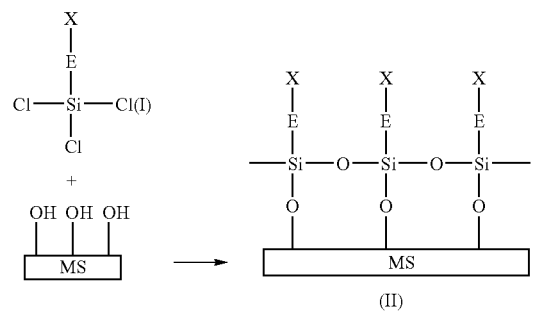

(II)

wherein X and E respond the definition which has been given above and MS represents a mineral substrate as has been described above.

The two-dimensional monolayer grafting of an isocyanate functionalized alkylsilane on a mineral substrate is new. Consequently, the Self Assembled Monolayer grafted substrate responding to formula (II) is another object of the invention. The formation of the SAM at the surface of glass slides or oxidized silicon wafers is demonstrated on the basis of surface analysis methods such as contact angle, Atomic Force Microscopy (AFM), ellipsometry, Attenuated Total Reflexion Fourier Transform Infrared spectroscopy (ATR FTIR) experiments. The characteristics and parameters of these measurements for a monolayer coverage, depending on the silane and on the surface, are well defined in the literature such as Ulman A. "An introduction to ultra thin organic films from Langmuir-Blodget to Self Assembly", Academic Press, London, 1991; or Ulman A., Chem. Rev., 1996, 96, 1533.

Concerning silica particle supports, the existence of a monolayer is demonstrated on the basis of solid state analysis methods such as micro-analysis, BET, solid-state NMR and FTIR experiments.

The method described above is reproducible.

Preferentially, it is observed that roughness is inferior or equal to 0.5 nm, even more preferably inferior or equal to 0.3 nm, and advantageously inferior or equal to 0.2 nm.

With regards to prior art methods which disclose the preparation of mineral substrates grafted by an isocyanate-comprising organosilane, the method of the invention has the following advantages: the grafting is bi-dimensional: a Si—O—Si link is built between neighbouring silane groups; aggregate formation is avoided, no catalyst is necessary.

The substrate of formula (II) bears O=C=N— functions bound to the mineral substrate (MS) by the intermediary of

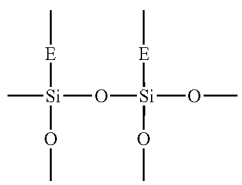

links. The O=C=N— functions are uniformly distributed on the substrate surface and are equally accessible.

Another object of the invention is the use of a substrate of formula (II) for the further grafting of a molecule comprising a nucleophile function, like an amine or a thiol or a hydroxyl function.

Said further grafting is operated by contacting the grafted substrate (II) with a solution of a molecule of formula HY-Z (III) in a solvent, wherein HY is a function which is reactive with isocyanate functions and Z is not.

For example HY can be selected among an amino function —NH$_2$, a thiol function —SH, a hydroxyl function —OH. Z can be any chemical group selected in such a manner as to confer to the substrate onto which it is grafted the physicochemical properties which it is desired to obtain. For example, Z can be an aromatic group with a choice of substituents, an aliphatic chain, substituted or not. Z can bear reactive functions which are protected by a labile protective group for further unmasking.

For example Z can be a parabromophenyl group, a paratolylgroup, a dodecyl chain, a $^t$BOC protecting group (tert-butyloxycarbonyl), or a Fmoc (fluorenomethyloxycarbonyl) group. Preferably the grafting of Y-Z on the grafted substrate (II) is conducted in an inert solvent, like for example trichloroethylene or dimethyl formamide.

Such a grafting can be depicted by scheme 2:

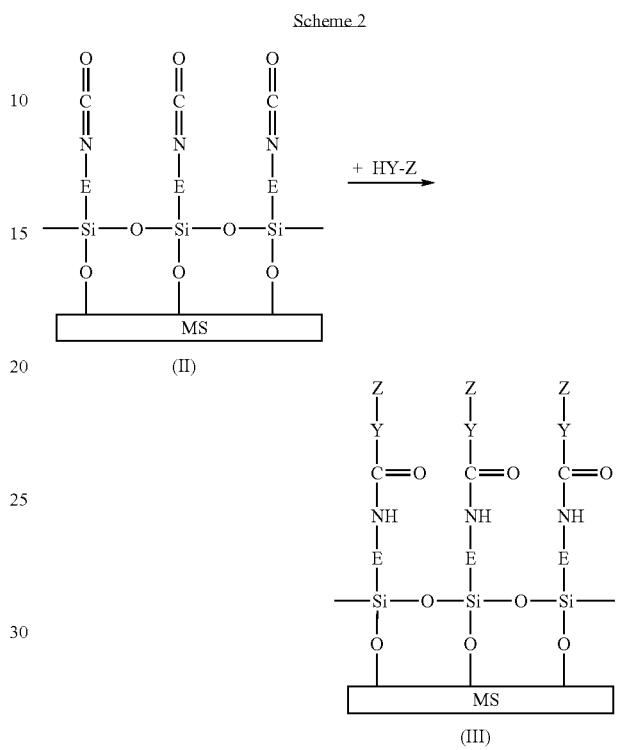

Another object of the invention is the Self Assembled Monolayer grafted substrate responding to formula (III), wherein Y is such that HY is a function which is reactive with isocyanate functions and Z is not:

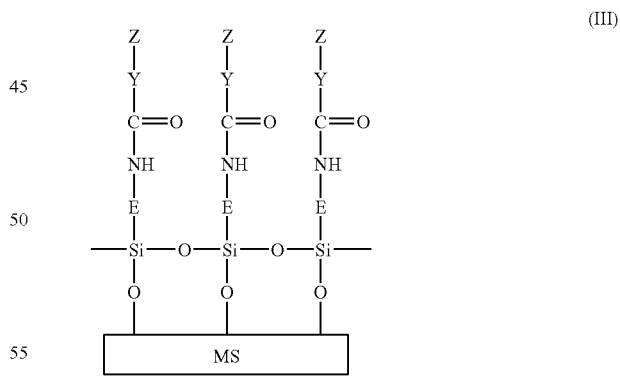

Preferably said grafting is performed in a solution of HY-Z in an appropriate solvent, at a concentration of HY-Z comprised between $10^{-2}$ mol/l and 1 mol/l, preferably between 0.05 and 0.5 mol/l.

The contacting of the substrate (II) with the solution of reactant HY-Z lasts between ½ hour and 8 hours, preferably between 1 hour and 6 hours, even more preferably between 2 hours and 4 hours.

Said reaction is preferably performed at a controlled temperature between 0 and 5° C. and under inert atmosphere.

Said reaction has the advantage that it can be performed without the help of any catalyst.

The grafting of a molecule Y-Z on the substrate of formula (II) gives a substrate covered with a monolayer which has the selected physicochemical properties corresponding to Y-Z. The regularity of grafting has been controlled by AFM, ATR FTIR, contact angle method and ellipsometry.

After attachment of the molecule Y-Z to the surface, the grafted substrate (III) can be used in assays for detection purposes where the Y-Z molecule is a probe. Suitable, but non-limiting examples of probes include a protein, a peptide, a nucleic acid, an amino acid, a peptide nucleic acid, a linked nucleic acid, a nucleoside triphosphate, a carbohydrate, a lipid, a lipid bound protein, an aptamer, a virus, a cell fragment, or a whole cell. The probe may have one or more reactive amino thiol or hydroxyl groups inherently as part of its structure or may be derivatized by any suitable means to include one or more of these reactive groups. In cases where an amino-containing oligonucleotide was used to prepare a device using the above method, the resulting immobilized oligonucleotides may be used in hybridization reactions with other nucleic acids. Oligonucleotide probes immobilized in the manner described above retain the ability to specifically recognize and bind target DNAs having complementary nucleotide sequences.

In another aspect of the invention, the immobilized molecules Y-Z bound to the silica surface may include a functional group, e.g., a carboxyl moiety. This functional group may be used to couple with a second molecule or probe. Hence, the immobilized molecule Y-Z may act as a spacer or a linker to bind a second molecule or probe to the silica surface. The second molecule includes a second functional group, e.g., an amino function, which allows it to react directly or indirectly with the immobilized molecules.

In practicing this invention, any desired Y-Z molecule may be used as a linker or spacer, provided that it has some functionality that allows the molecule to covalently attach to another molecule, alone or in the presence of one or more coupling agents. Any suitable concentration of second molecules may be used in any suitable solvent or solvent mixture as described above. Similarly, any suitable method of applying the solution including the second molecules may be used as described above.

EXPERIMENTAL PART

A

Preparation of 10-Isocyanatodecyltrichlorosilane

To a solution of 5.10 g of 10-decenylisocyanate in 5.60 ml trichlorosilane is added drop-wise, under inert atmosphere 300 µl of Karstedt's catalyst while stirring. The reaction is exothermic and the mixture turns yellows. After 2 hours excess trichlorosilane is evaporated, and the residue is distillated under vacuum.

8.4 g (94% yield) of 10-isocyanatodecyltrichlorosilane are obtained.

$^1$H NMR (200 MHz, CDCl$_3$): 1.34-1.47 (m, 14H); 1.54-1.71-(m, 4H); 3.31 (t, 3J=6.5 Hz, 2H).

$^{13}$CNMR (50 MHz, CDCl$_3$): 22.29 (t, 1C, CH$_2$); 24.70 (t, 1C, CH$_2$); 26.82 (t, 1C, CH$_2$); 29.31 (t, 1C, CH$_2$); 29.36 (t, 1C, CH$_2$); 29.62 (t, 1C, CH$_2$); 29.79 (t, 1C, CH$_2$); 31.70 (t, 1C, CH$_2$); 32.17 (t, 1C, CH$_2$); 43.38 (t, 1C, CH$_2$); 122.36 (s, 1C, N=C=O).

IR (CH$_2$Cl$_2$): 2930 (ν CH), 2856 (ν CH), 2225 (ν N=C=O), 1488, 1466, 1056.

High Resolution Mass: (M+HCl)$^+$: C$_{11}$H$_{22}$ONCl$_4$Si: calc: 352.0275.

B

Grafted Silicon Substrates

A series of silicon substrates covered with an organic layer has been prepared by treatment with isocyanatodecyltrichlorosilane and further grafting with several organic molecules.

EXAMPLE 1

Grafting with P-toluidine

Substrate: silicon discs (1, 0, 0) cut to give rectangular plaques of dimension 1×2 cm$^2$.

Process: In a first step each plaque has been immersed in a solution of concentrated HF for a few seconds, until the surface has become hydrophobic. Then each plaque has been rinsed with ultrapure water and treated by ozone under UV.

Each plaque has been introduced into a Schlenk tube comprising 20 ml of a 10$^{-2}$ M solution of isocyanato decyl trichlorosilane and 10$^{-1}$ M of diisopropylethyl amine in trichloroethylene. The whole was kept at 0° C. for 1 hour in the absence of any stirring under Argon atmosphere.

After 1 hour, the solution is removed and the plaques are washed twice with trichloroethylene for 5 minutes at a temperature of 0° C. under argon. Then a 10$^{-1}$ M solution of p-toluidine in trichloroethylene comprising 0.1 mL of ethanol is added in the tube. The plaque remains there for 3 hours at a temperature of 0° C. in the absence of any stirring, under argon.

After 3 hours, the plaques are removed from the tube, washed with trichloroethylene, then with ethanol and further with chloroform, each washing being done with ultrasound treatment for about 5 minutes. The plaques thus obtained can be kept under ambient atmosphere without any degradation.

The contact angle at the surface of the plaques, measured by the method of the drop at equilibrium is 83±1°, which proves that the surface is homogeneous and hydrophobic.

An ATR infrared spectroscopy shows a vibration band at 2 273 cm$^{-1}$, characteristic of the isocyanate function. This signal disappears 30 minutes after the introduction of p-toluidine. During the chlorosilane grafting, vibrations which are characteristic of the aliphatic chain can be observed:

|  | OCN—C$_{10}$H$_{20}$—SiCl$_3$ grafted | OCN—C$_{10}$H$_{20}$—SiCl$_3$ In solution |
| --- | --- | --- |
| ν$_{as}$ CH$_2$ | 2925 cm$^{-1}$ | 2931 cm$^{-1}$ |
| ν$_{as}$ CH$_2$ | 2854 cm$^{-1}$ | 2858 cm$^{-1}$ |

The transfer of the aliphatic signal demonstrates an organized grafting at the surface of the plaque.

AFM images show an homogeneous surface with reduced rugosity of about 0.14 nm.

The thickness of the layers obtained by the process of the invention has been determined by ellipsometry by using n=1.45 as a refraction index. This thickness is of about 2.3 nm.

EXAMPLES 2 TO 7

The same protocol has been repeated with other plaques and using the following grafting in replacement of p-toluidine:

Example 2: p-anisidine,
Example 3: tert-butylcarbazate,
Example 4: Fmoc-hydrazine,
Example 5: 1-dodecanethiol (ethanol has been replaced by triethylamine),
Example 6: p-bromothiophenol (triethylamine has been used instead of ethanol).
Example 7: p-methoxyphenol The same analyses have been performed on the resulting plaques. The corresponding results are gathered in the tables 1 and 2 hereunder:

TABLE 1

|  | Y-Z | Contact angle | Roughness | Layer's thickness |
|---|---|---|---|---|
| Example 1 | p-toluidine | 83° ± 1 | 0.14 nm | 2.3 nm |
| Example 2 | p-anisidine | 77° ± 2 | 0.17 nm | 2.3 nm |
| Example 3 | NH$_2$—NH—BOC | 80° ± 1 | 0.17 nm | 1.8 nm |
| Example 4 | NH$_2$—NH-Fmoc | 83° ± 1 | 0.23 nm | 2.2 nm |
| Example 5 | 1-dodecanethiol | 89° ± 1 | 0.16 nm | 2.5 nm |
| Example 6 | p-bromothiophenol | 83° ± 1 | 0.19 nm | 2.2 nm |
| Example 7 | p-methoxyphenol | 78° ± 2 | 0.17 nm | 2.2 nm |

TABLE 2

|  | Y-Z | Time of disappearance of the NOC signal | Vibration signal characteristic of Y-Z | Vibration signal characteristic of N—(CO)—Y |
|---|---|---|---|---|
| Example 1 | p-toluidine | 30 min | — | ν N—(CO)—N = 1 645 cm$^{-1}$ |
| Example 2 | p-anisidine | 15 min | — | ν N—(CO)—N = 1 646 cm$^{-1}$ |
| Example 3 | NH$_2$—NH—BOC | 10 min | ν N—(CO)—O = 1 725 cm$^{-1}$<br>ν CH$_3$ = 2 962 cm$^{-1}$ | ν N—(CO)—N = 1 660 cm$^{-1}$ |
| Example 4 | NH$_2$—NH-Fmoc | 15 min | — | — |
| Example 5 | 1-dodecanethiol | 45 min | ν CH$_3$ = 2 962 cm$^{-1}$<br>ν CH$_3$ = 2 875 cm$^{-1}$ | ν N—(CO)—S = 1 650 cm$^{-1}$ |
| Example 6 | p-bromothiophenol | 3 min | — | ν N—(CO)—S = 1 669 cm$^{-1}$ |
| Example 7 | p-methoxyphenol | 20 min. | ν CH$_3$ = 2 969 cm$^{-1}$ | ν N—(CO)—O = 1 707 cm$^{-1}$ |

The invention claimed is:

1. A method for preparing a device comprising a mineral support (MS) and bound thereto a Self Assembled Monolayer (SAM) of molecules having formula (Ibis):

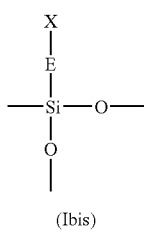

(Ibis)

wherein:
X represents an isocyanate function —N=C=O,
E represents a straight alkyl chain comprising from 8 to 30 carbon atoms, and optionally comprises a bridge function selected from the group consisting of: —O—, —S—, —NH—, —COO—, and aryl;
and X and Si are separated by a chain of at least 8 carbon atoms,
wherein said method comprises the steps of reacting a mineral substrate (MS) comprising hydroxyl functions on its surface with a molecule of formula (I):

in an aprotic solvent in the presence of a Lewis base.

2. The method of claim 1, wherein the Lewis base is selected from the group consisting of triethylamine and diisopropylethylamine.

3. The method of claim 1, wherein the hydroxyl functions are silanol functions.

4. The method of claim 1, wherein the aprotic solvent is selected from the group consisting of carbon tetrachloride, trichloroethylene, and toluene.

5. The method of claim 1, wherein the mineral substrate comprising hydroxyl functions on its surface is selected from the group consisting of wafer-type silicon covered by a layer of silica or a piece of glass.

6. The method of claim 5, wherein the mineral substrate is submitted to a treatment selected from the group consisting of:

immersing the substrate in a HF aqueous solution with a HF concentration of at least 10%, while submitting it to ultrasound treatment, rinsing with water followed by ozone treatment under UV;

submitting the substrate to an oxygen flow at an elevated temperature;

submitting the substrate to a chemical basic oxidation; and submitting the substrate to a chemical acidic oxidation.

7. The method of claim 1, wherein the organotrichlorosilane is solubilized in an aprotic solvent with a concentration comprised between 10$^{-3}$ to 10$^{-1}$ mol/l.

8. The method of claim 2, wherein the substrate is immersed for a length of time of 15 minutes to 3 hours in the organotrichlorosilane solution comprising DIEA, under controlled temperature and under inert atmosphere.

9. A method of detecting a target molecule or screening interaction with other molecules or both, which comprises the step of:

a) contacting the self-assembled monolayer grafted substrate of the following formula (III):

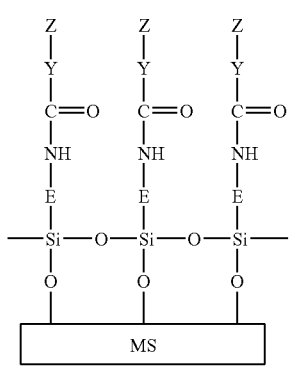 (III)

with a sample, in the presence of a Lewis base; and
b) determining whether the target molecule is present in the sample or said interaction with other molecules in the sample occurs or both by detecting said target molecule or said interaction with other molecules in the sample;

and wherein in the formula (III), the moiety -Y-Z is a probe, E is a straight alkyl chain comprising from 8 to 30 carbon atoms, and MS is a mineral substrate comprising hydroxyl functions on its surface.

10. The method of claim 9, wherein in the self-assembled monolayer grafted substrate of the formula (III), the probe -y-Z is selected from the group consisting of p-toluidine, p-anisidine, tert-butylcarbazate, Fmoc-hydrazine, 1-dodecanethiol and p-bromothiophenol.

11. The method of claim 9, wherein in the self-assembled monolayer grafted substrate of the formula (III), the probe -y-Z is selected from the group consisting of a protein, a peptide, a nucleic acid, an amino acid, a peptide nucleic acid, a linked nucleic acid, a nucleoside triphosphate, a carbohydrate, a lipid, a lipid bound protein, an aptamer, a virus, a cell fragment and whole cell.

12. The method of claim 9, wherein the Lewis base is selected from the group consisting of triethylamine and diisopropylethylamine.

* * * * *